United States Patent [19]

Grohe et al.

[11] 3,932,436
[45] Jan. 13, 1976

[54] 2-THIAZOLONE-5-CARBOXYLIC ACID ESTER FUNGICIDAL AGENTS

[75] Inventors: Klaus Grohe, Cologne; Paul-Ernst Frohberger, Leverkusen, both of Germany

[73] Assignee: Bayer Aktiengesellschaft, Leverkusen, Germany

[22] Filed: Oct. 26, 1973

[21] Appl. No.: 410,073

[30] Foreign Application Priority Data
Oct. 28, 1972  Germany............................ 2253027

[52] U.S. Cl............................ 260/306.7 R; 424/270
[51] Int. Cl.²...................................... C07D 277/22
[58] Field of Search ............................ 260/306.7 R

[56] References Cited
UNITED STATES PATENTS
2,678,929   5/1954   Grundy et al................. 260/306.7 R
FOREIGN PATENTS OR APPLICATIONS
2,137,649   2/1973   Germany..................... 260/306.7 R OTHER PUBLICATIONS
Grohe and Heitzer, Ann., 1973 (5–6), pp. 1018–1024.

*Primary Examiner*—Richard J. Gallagher
*Attorney, Agent, or Firm*—Burgess, Dinklage & Sprung

[57] ABSTRACT

Fungicidal compositions containing, and methods of combating fungi using, 2-thiazolone-5-carboxylic acid ester fungicidal agents of the formula

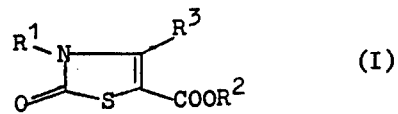

in which
R¹ is hydrogen; alkyl of up to 12 carbon atoms optionally substituted by phenyl, halophenyl or alkylphenyl with up to three carbon atoms in each alkyl radical; cyclopentyl; cyclohexyl; aryl; haloaryl; or alkylaryl with up to three carbon atoms in each alkyl radical, R² is cyclopentyl; cyclohexyl; alkyl of up to 18 carbon atoms optionally substituted by cyclopentyl, cyclohexyl, lower alkoxy, phenoxy, nitrile, lower alkoxycarbonyl, phenyl, halophenyl or alkylphenyl, and R³ is hydrogen, trihalomethyl, lower alkoxycarbonyl, aryl, haloaryl, alkylaryl, or any of the radical set forth for R², display strong fungicidal properties.

3 Claims, No Drawings

2-THIAZOLONE-5-CARBOXYLIC ACID ESTER FUNGICIDAL AGENTS

The present invention relates to and has for its objects the provision of particular compositions for, and methods of, combating fungi using 2-thiazolone-5-carboxylic acid esters, with other and further objects becoming apparent from a study of the within specification and accompanying examples.

It has been disclosed in U.S. Pat. No. 2,457,674 that zinc ethylene-1,2-bis-dithiocarbamate (Compound A) can be used as a fungicide. However, if small amounts are used, the fungicidal activity of this substance is not always completely satisfactory.

It has now been found that 2-thiazolone-5-carboxylic acid esters of the general formula

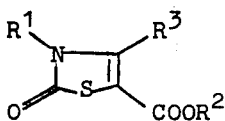

(I)

in which
R$^1$ is hydrogen; alkyl of up to 12 carbon atoms optionally substituted by phenyl, halophenyl or alkylphenyl with up to three carbon atoms in each alkyl radical; cyclopentyl; cyclohexyl; aryl; haloaryl; or alkylaryl with up to three carbon atoms in each alkyl radical,
R$^2$ is cyclopentyl; cyclohexyl; alkyl of up to 18 carbon atoms optionally substituted by cyclopentyl, cyclohexyl, lower alkoxy, phenoxy, nitrile, lower alkoxycarbonyl, phenyl, halophenyl or alkylphenyl, and
R$^3$ is hydrogen, trihalomethyl, lower alkoxycarbonyl, aryl, haloaryl, alkylaryl, or any of the radical set forth for R$^2$,
display strong fungicidal properties.

Suprisingly, the 2-thiazolone-5-carboxylic acid esters to be used according to the invention display a substantially higher fungicidal action than the zinc ethylene-1,2-bis-dithiocarbamate known from the state of the art. The active compounds which can be used according to the invention thus represent an enrichment of the art.

R$^1$ preferably represents hydrogen or optionally substituted straight-chain or branched alkyl with one to eight carbon atoms. As substituents of the alkyl radical there may in particular be mentioned: phenyl and phenyl which is monosubstituted or polysubstituted by fluorine, chlorine, bromine or methyl. Alternatively, R$^1$ preferably represents cyclohexyl or cyclopentyl, or phenyl, and the latter can in turn be monosubstituted or polysubstituted by fluorine, chlorine, bromine or methyl. Alternatively, R$^1$ preferably represents naphthyl.

R$^2$ preferably represents cyclohexyl or cyclopentyl or optionally substituted straight-chain or branched alkyl with one to 12 carbon atoms, and the alkyl radical can preferably be substituted by cyclopentyl, by cyclohexyl, by alkoxy with up to four carbon atoms, especially methoxy or ethoxy, by phenoxy, by nitrile, by alkoxycarbonyl with one to four carbon atoms or by phenyl, and the latter can in turn be monosubstituted or polysubstituted, preferably by fluorine, chlorine, bromine or methyl.

R$^3$ preferably represents those radicals which have also been mentioned preferentially for R$^2$. Alternatively, R$^3$ preferably represents hydrogen, trihalomethyl, especially trichloromethyl or trifluoromethyl, alkoxycarbonyl with 1 to 4 carbon atoms, especially methoxycarbonyl or ethoxycarbonyl, or phenyl which can in turn be monosubstituted or polysubstituted, preferably by fluorine, chlorine, bromine or methyl. Alternatively, R$^3$ preferably represents naphthyl.

The following are specific examples of active compounds of the formula (I) for use according to the invention:

3-methyl-4-methyl-2-thiazolone-5-carboxylic acid ethyl ester,
3-benzyl-4-methyl-2-thiazolone-5-carboxylic acid ethyl ester,
4-methyl-2-thiazolone-5-carboxylic acid ethyl ester,
4-methyl-2-thiazolone-5-carboxylic acid isopropyl ester,
4-methyl-2-thiazolone-5-carboxylic acid (β-phenyl)-ethyl ester,
4-methyl-3-phenyl-2-thiazolone-5-carboxylic acid ethyl ester,
4-methyl-3-phenyl-2-thiazolone-5-carboxylic acid methyl ester,
4-methyl-2-thiazolone-5-carboxylic acid n-dodecyl ester,
3-(2,6-dichlorophenyl)-4-methyl-2-thiazolone-5-carboxylic acid ethyl ester,
4-carbethoxy-3-phenyl-2-thiazolone-5-carboxylic acid ethyl ester,
4-methyl-2-thiazolone-5-carboxylic acid benzyl ester,
4-methyl-2-thiazolone-5-carboxylic acid n-butyl ester,
4methyl-2-thiazolone-5-carboxylic acid cyclohexyl ester,
4-methyl-2-thiazolone-5-carboxylic acid methyl ester,
4-trichloromethyl-2-thiazolone-5-carboxylic acid methyl ester,
4-methyl-2-thiazolone-5-carboxylic acid cyclohexylmethyl ester,
4-methyl-2-thiazolone-5-carboxylic acid (β-ethoxy)-ethyl ester,
4-methyl-2-thiazolone-5-carboxylic acid (β-isopropoxy)-ethyl ester,
4-methyl-2-thiazolone-5-carboxylic acid sec.-butyl ester,
4-methyl-2-thiazolone-5-carboxylic acid n-hexyl ester,
4-methyl-2-thiazolone-5-carboxylic acid (β-cyano)-ethyl ester,
4-methyl-2-thiazolone-5-carboxylic acid n-decyl ester,
4-methyl-2-thiazolone-5-carboxylic acid (β-phenoxy)-ethyl ester,
3-methyl-4-methyl-2-thiazolone-5-carboxylic acid cyclohexyl ester,
3-phenyl-4-methyl-2-thiazolone-5-carboxylic acid cyclohexyl ester,
3-cyclohexyl-4-methyl-2-thiazolone-5-carboxylic acid ethyl ester, 3-cyclopentyl-4-methyl-2-thiazolone-5-carboxylic acid ethyl ester,
4-methyl-3-(2-methylphenyl)-2-thiazolone-5-carboxylic acid ethyl ester,
4-methyl-3-naphthyl-2-thiazolone-5-carboxylic acid methyl ester,
4-methyl-2-thiazolone-5-carboxylic acid (β-2,6-dichlorophenyl)-ethyl ester,
4-phenyl-2-thiazolone-5-carboxylic acid methyl ester,
4-naphthyl-2-thiazolone-5-carboxylic acid ethyl ester,
3-methyl-4-(2,6-dichlorophenyl)-2-thiazolone-5-carboxylic acid ethyl ester,
3-methyl-4-naphthyl-2-thiazolone-5-carboxylic acid ethyl ester,
3-methyl-2-thiazolone-5-carboxylic acid ethyl ester,
4-hexyl-3-methyl-2-thiazolone-5-carboxylic acid ethyl ester,
3-hexyl-4-methyl-2-thiazolone-5-carboxylic acid ethyl ester,
4-methyl-2-thiazolone-5-carboxylic acid octadecyl ester,
4-trifluoromethyl-2-thiazolone-5-carboxylic acid ethyl ester,
4-(4'-fluorophenyl)-2-thiazolone-5-carboxylic acid ethyl ester,
4-(4'-methylphenyl)-2-thiazolone-5-carboxylic acid 4-fluorophenylethyl ester,
3-(4'-bromophenylpentyl)-4-cyclohexyl-2-thiazolone-5-carboxylic acid ethyl ester,
3-methoxyethyl-4-methyl-2-thiazolone-5-carboxylic acid ethyl ester,
4-methyl-2-thiazolone-5-carboxylic acid (-β-n-butoxy) ethyl ester,
4-(4'-chlorobenzyl)-2-thiazolone-5-carboxylic acid ethyl ester,
and the like.

Amongst the 2-thiazolone-5-carboxylic acid esters of the formula (I) which can be used according to the invention, only 4-methyl-2-thiazolone-5-carboxylic acid ethyl ester has previously been known [compare Proc. Indian Acad. Sci. 22A, 362–378(1945) and J. Pharm. Soc. Japan 76, 301 – 305 (1956)]. The remainder of the compounds which can be used according to the invention are new. They can be prepared as described in U.S. Patent application Ser. No. 271,104, filed July 12, 1972, now pending, the disclosure of which is incorporated herein by reference. As described there the substances of the formula (I) are obtained when β-aminoacrylic acid esters of the general formula

in which
R$^1$, R$^2$ and R$^3$ have the abovementioned meanings,
are reacted with chlorocarbonylsulfenyl chloride of the formula

optionally in the presence of an inert diluent and optionally in the presence of an acid-binding agent, at temperatures from 0° to 200°C.

The β-aminoacrylic acid esters of the formula (II) used as the starting material are known. They can be manufactured in a simple manner by reaction of acylacetic esters with ammonia and primary amines [compare Organicum, Organisch Chem. Grundpraktikum VEB Deutscher Verlag d. Wissenschaften, Berlin, page 354 (1964); J. Amer. Chem. Soc. 68, 514 (1946)], by reaction of Grignard compounds with cyanoacetic esters [compare Collection of Czechoslovakian Chemical Communications 25, 607 (1960)], by reaction of propiolic acid esters and acetylenedicarboxylic esters with ammonia or primary amines [compare Monatshefte fuer Chemie 36, 109 (1915); Chem. Ber. 99, 2,526 (1966); Nippon Kagaku Zasshi 82, 632 (1961)] and by reaction of trichloroacetonitrile with acetoacetic acid methyl ester [compare I. Prakt. Chem. [4] 27, 239 (1965)].

The following may be mentioned as examples of the β-aminoacrylic acid esters of the formula (II) which can be used as starting materials: β-aminocrotonic acid methyl ester, β-aminocrotonic acid ethyl ester, β-aminocrotonic acid i-propyl ester, β-aminocrotonic acid n-dodecyl ester, β-aminocrotonic acid benzyl ester, β-aminocrotonic acid cyclohexyl ester, β-aminocrotonic acid β-phenethyl ester, β-methylaminocrotonic acid ethyl ester, β-anilinocrotonic acid ethyl ester, β-benzylaminocrotonic acid ethyl ester, β-aminocinnamic acid ethyl ester, β-amino-β-ethyl-acrylic acid ethyl ester and β-methylaminocinnamic acid ethyl ester.

Chlorocarbonylsulfenyl chloride of the formula (III) is known and easily prepared. It can be obtained in a simple manner by reaction of trichloromethanesulfenyl chloride with concentrated sulfuric acid (Synthesis 1970, 567).

The reaction of β-aminoacrylic acid esters of the formula (II) with chlorocarbonylsulfenyl chloride of the formula (III) is carried out at temperatures of 0° to 200°C, preferably at 10° to 150°C.

In general, the β-aminoacrylic acid ester of the formula (II) and the chlorocarbonylsulfenyl chloride are heated in a molar ratio of 1:1 to 1:2, preferably in an inert solvent, at 30°C to 200°C, preferably 30° to 150°C, until the evolution of HCl ceases. As a rule, the reaction is complete after 1 to 4 hours.

All customary acid-binding agents can be used as acid binders. These include, for example, bases such as pyridine or calcium carbonate.

Possible inert solvents are hydrocarbons or chlorinated hydrocarbons, for example benzene, toluene, chlorobenzene, o-dichlorobenzene or carbon tetrachloride, as well as sulpholane or dioxane.

The reaction products may be isolated by filtering off the precipitate which has separated out or stripping off the solvent under reduced pressure and either distilling or recrystallizing the residue which remains.

The active compounds to be used according to the invention possess strong fungitoxic properties and can therefore be used for combating harmful fungi. In addition to their high effectiveness, these compounds also show a broad spectrum of action and possess a relatively low toxicity towards warm-blooded animals. This makes them harmless to handle. Because of their low phytotoxicity they are in particular suitable for combating fungal diseases of plants. Fungitoxic agents are employed in plant protection for combating fungi from the most diverse classes of fungus, such as Archimycetes, Phycomycetes, Ascomycetes, Basidiomycetes and Fungi Imperfecti.

The active compounds are particularly suitable for seed dressings and also for the treatment of soil. Their action is above all directed against seed-borne fungi. Bunt diseases of cereals, for example bunt of wheat, should be mentioned especially.

The active compounds according to the instant invention can be utilized, if desired, in the form of the usual formulations or compositions with conventional inert (i.e., plant compatible or herbicidally inert) pesticide diluents or extenders, i.e., diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alimina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides, or insecticides, acaricides, rodenticides, bactericides, nematocides, herbicides, fertilizers, growth-regulating agents, plant nutrients, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprises mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e., mist form, for example by airplane crop spraying techniques. Only up to at most about a few liters/hectare are needed, and often amounts only up to about 15 to 1,000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used for seed dressing, amounts of active compound of 50 mg to 50g, preferably of 200 mg to 10 g, are generally used per kilogram of seed.

In the case of soil treatment, which can be carried out over the entire surface of the soil, or in strips or at points, active compound concentrations of 1 to 500 g of active compound per $m^3$ of soil, preferably 10 to 200 g per $m^3$, are generally required at the place of the desired action.

Furthermore, the present invention contemplates methods of selectively killing, combating or controlling pests, e.g. insects, acarids, fungi, bacteria and yeasts, and more particularly methods of combating at least one of insects and acarids, which comprises applying to at least one of correspondingly (a) such insects, (b) such acarids, (c) such fungi, (d) such bacteria, (e) such yeasts, and (f) the corresponding habitat thereof, i.e., the locus to be protected, a correspondingly combative or toxic amount, i.e., an insecticidally, acaricidally, fungicidally, bactericidally or yeasticidally effective amount of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, slurry dressing, moist dressing, wet dressing, and the like.

It will be realized, of course, that the concentration of the particular active compound utilized in admixture with the carrier vehicle will depend upon the intended application. Therefore, in special cases it is possible to go above or below the aforementioned concentration ranges.

The synthesis, unexpected superiority and outstanding activity of the 2-thiazolone-5carboxylic acid esters which can be used according to the present invention are illustrated, without limitation, by the following examples:

EXAMPLE 1

Seed dressing test/bunt of wheat (seed-born mycosis)

To produce a suitable dry dressing, the active compound was extended with a mixture of equal parts by weight of talc and kieselguhr to give a finely powdered mixture with the desired concentration of the active compound.

Wheat seed was contaminated with 5g of the chlanydospores of *Tilletia caries* per kg of seed. To apply the dressing, the seed was shaken with the dressing in a closed glass flask. The seed, on moist loam under a cover of a layer of muslin and 2 cm of moderately moist compost soil, was exposed to optimum germination conditions for the spores for 10 days at 10°C in a refrigerator.

The germination of the spores on the wheat grains, each of which was contaminated with about 100,000 spores, was subsequently determined microscopically. The smaller the number of spores which has germinated, the more effective was the compound.

The active compounds, the concentrations of the active compounds in the dressing, the amounts of dressing used and the percentage spore germination can be seen from the following Table 1:

EXAMPLE 2

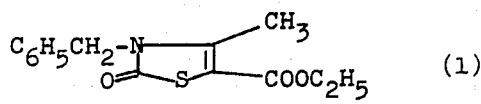

(1)

109.5 g (0.5 mole) of β-benzylaminocrotonic acid ethyl ester were added dropwise to 72 g (0.55 mole) of chlorocarbonylsulfenyl chloride and 120 ml of dry chlorobenzene at 10°C to 20°C, while cooling with ice. Thereafter the mixture was heated to 80°C – 90°C for about one hour, in the course of which vigorous evolution of hydrogen chloride occurred. The mixture was heated to the boil until the evolution of gas had ceased, and was filtered hot, and the solvent was stripped off in a water pump vacuum. The oil which remained was subjected to a fractional high vacuum distillation. 91 g (66% of theory) of 3-benzyl-4-methyl-2-thiazolone-5-carboxylic acid ethyl ester of boiling point 197° – 199°C/0.5 mm Hg were obtained.

EXAMPLE 3

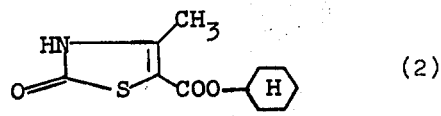

(2)

72 g (0.55 mole) of chlorocarbonylsulfenyl chloride were initially introduced into 100ml of dry chloroben- Table 1

Seed dressing test/bunt of wheat

| Active compound | | Active compound concentration in the dressing in % by weight | Amount of dressing used in g/kg of seed | Spore germination in % |
|---|---|---|---|---|
| without dressing | | – | – | >10 |
| 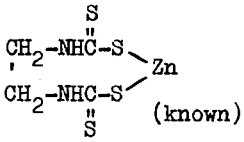 (known) | (A) | 10 | 1 | 5 |
| 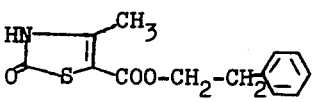 | (6) | 10 | 1 | 0.005 |
| 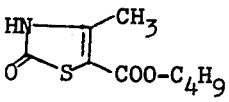 | (13) | 10 | 1 | 0.005 |
| 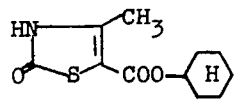 | (2) | 10<br>3<br>1 | 1<br>1<br>1 | 0.005<br>0.005<br>0.5 | zene. 91.5 g (0.5 mole) of β-aminocrotonic acid cyclohexyl ester were added dropwise while cooling with ice and stirring. The mixture was carefully heated to the boil, in the course of which the evolution of hydrogen chloride was not allowed to become too vigorous, and was then boiled under reflux until the evolution of gas had ceased. The solvent was distilled off in vacuo and the residue was recrystallized from a little glycol monoethyl ether acetate. 72.5 g (60% of theory) of 4-methyl-2-thiazolone-5-carboxylic acid cyclohexyl ester of melting point 131°C were obtained.

The compounds of the general formula

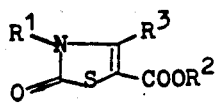
(I)

identified in the following Table 2 were obtained in a similar manner.

$R^3$ is methyl only, whereas $R^2$ is a hydrocarbon group with four to eight carbon atoms, such as alkyl with four to eight carbon atoms, cyclohexyl, cyclohexylmethyl (i.e., hexahydrobenzyl), cyclohexylethyl and phenylethyl, show a remarkable good activity. The following new compounds are given as an example:

4-methyl-2-thiazolone-5-carboxylic acid n-butyl ester,
4-methyl-2-thiazolone-5-carboxylic acid n-hexyl ester
4-methyl-2-thiazolone-5-carboxylic acid cyclohexyl ester,
4-methyl-2-thiazolone-5-carboxylic acid cyclohexylmethyl ester,
4-methyl-2-thiazolone-5-carboxylic acid cyclohexylethyl ester,
4-methyl-2-thiazolone-5-carboxylic acid phenylethyl ester.

What is claimed is:

1. 2-thiazolone-5-carboxylic esters of the formula

Table 2

| Compound No. | $R_1$ | $R_2$ | $R_3$ | Melting point (°C) Boiling point/ mm Hg | Yield (% of theory) |
|---|---|---|---|---|---|
| 3 | $CH_3$ | $C_2H_5$ | $CH_3$ | 62 – 63 | 82 |
| 4 | H | $C_2H_5$ | $CH_3$ | 178 | 75 |
| 5 | H | $(CH_3)_2CH$ | $CH_3$ | 136 | 60 |
| 6 | H | $C_6H_5CH_2CH_2$ | $CH_3$ | 141 | 55 |
| 7 | $C_6H_5$ | $C_2H_5$ | $CH_3$ | 92 – 94 | 75 |
| 8 | $C_6H_5$ | $CH_3$ | $CH_3$ | 139 | 78 |
| 9 | H | n—$C_{12}H_{25}$ | $CH_3$ | 94 | 70 |
| 10 | 2,6-Cl$_2$C$_6$H$_3$ | $C_2H_5$ | $CH_3$ | 92 | 65 |
| 11 | $C_6H_5$ | $C_2H_5$ | $COOC_2H_5$ | 56 – 58 | 74 |
| 12 | H | $C_6H_5CH_2$ | $CH_3$ | 132 | 45 |
| 13 | H | n—$C_4H_9$ | $CH_3$ | 96 | 65 |
| 14 | H | $CH_3$ | $CH_3$ | 210 | 58 |
| 15 | H | $CH_3$ | $CCl_3$ | 128 | 42 |
| 16 | H | $CH_2$—C$_6$H$_{11}$ | $CH_3$ | 137 | 85 |
| 17 | H | $C_2H_5$—O—$(CH_2)_2$ | $CH_3$ | 89 | 60 |
| 18 | H | $(CH_3)_2CH$—O—$(CH_2)_2$ | $CH_3$ | 96 | 80 |
| 19 | H | $(CH_3)_2CH$—$CH_2$ | $CH_3$ | 122 | 76 |
| 20 | H | $CH_3(CH_2)_5$ | $CH_3$ | 94 | 84 |
| 21 | H | NC—$CH_2$—$CH_2$ | $CH_3$ | 143 | 30 |
| 22 | H | $CH_3$—$(CH_2)_9$ | $CH_3$ | 96 | 88 |
| 23 | H | $C_6H_5$—O—$(CH_2)_2$ | $CH_3$ | 155 | 85 |
| 24 | $CH_3$ | C$_6$H$_{11}$— | $CH_3$ | 86 | 90 |
| 25 | $C_6H_5$ | C$_6$H$_{11}$— | $CH_3$ | 135 | 65 |
| 26 | $C_6H_5CH_2$ | $C_2H_5$ | $CH_3$ | 199/0.5 | 66 |
| 27 | H | $CH_3(CH_2)_{17}$ | $CH_3$ | 105 | 80 |
| 28 | H | $C_2H_5$ | $CH_3(CH_2)_{16}$ | 42 | 75 |
| 29 | $CH_3$ | $CH_3$ | $(CH_3)_2CH$—O—$(CH_2)_2$ | 174/0.3 | 65 |
| 30 | $CH_3O(CH_2)_2$ | $CH_3$ | $C_2H_5$ | 65 | 85 |
| 31 | $C_6H_5$ | $CH_3$ | $(CH_3)_2CH$—O—$(CH_2)_2$ | 72 | 75 |
| 32 | H | $CH_3$ | n—$C_4H_9$—O—$(CH_2)_2$ | 70 | 60 |
| 33 | H | $CH_3$ | n—$C_3H_7$—O—$(CH_2)_2$ | 69 | 65 |
| 34 | H | $CH_3$ | $CH_3$—CH—$(CH_2)_2$  OCH$_3$ | 84 | 78 |

It will be appreciated that the instant specification and examples are set forth by way of illustration and not limitation, and that various modifications and changes may be made without departing from the spirit and scope of the present invention.

It should be noted that these new compounds, in which $R^1$ of the general formula is hydrogen only and

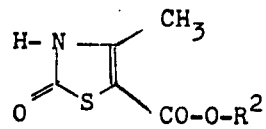

in which

R² is alkyl of four to eight carbon atoms, cyclohexyl, cyclohexylmethyl, cyclohexylethyl or phenyl ethyl.

2. A compound according to claim 1, wherein the ester is:
  4-methyl-2-thiazolone-5-carboxylic acid n-butyl ester,
  4-methyl-2-thiazolone-5-carboxylic acid n-hexyl ester,
  4-methyl-2-thiazolone-5-carboxylic acid cyclohexyl ester,
  4-methyl-2-thiazolone-5-carboxylic acid cyclohexylmethyl ester,
  4-methyl-2-thiazolone-5-carboxylic acid cyclohexylethyl ester,
  4-methyl-2-thiazolone-5-carboxylic acid phenylethyl ester.

3. A compound according to claim 1, wherein the ester is 4-methyl-2-thiazolone-5-carboxylic acid phenethyl ester of the formula

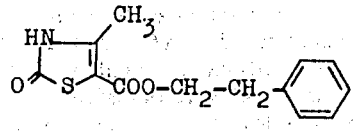

* * * * *